(12) United States Patent
Carina et al.

(10) Patent No.: US 6,617,299 B1
(45) Date of Patent: *Sep. 9, 2003

(54) COMPOSITION AND METHOD FOR BLEACHING A SUBSTRATE

(75) Inventors: Riccardo Filippo Carina, Les Ulis (FR); Bernard Lucas Feringa, Groningen (NL); Ronald Hage, Vlaardingen (NL); Catherine Hemmert, Toulouse (FR); Jean Hypolites Koek, Vlaardingen (NL); Rene Marcel LaCrois, Groningen (NL); Bernard Meunier, Toulouse (FR); Michael Renz, Toulouse (FR); Johannes Gerhardus Roelfes, Groningen (NL); Ebe Pieter Schudde, Groningen (NL); Rob Thijssen, Vlaardingen (NL); Robin Stefan Twisker, Vlaardingen (NL); Charon Zondervan, Groningen (NL)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/539,756

(22) Filed: Mar. 31, 2000

(30) Foreign Application Priority Data

| Apr. 1, 1999 | (GB) | 9907713 |
|---|---|---|
| Apr. 1, 1999 | (GB) | 9907714 |
| Sep. 1, 1999 | (WO) | PCT/GB99/02876 |
| Sep. 1, 1999 | (WO) | PCT/GB99/02878 |
| Feb. 29, 2000 | (GB) | 0004850 |

(51) Int. Cl.$^7$ ............... C11D 3/395; C11D 7/54; D06L 3/02

(52) U.S. Cl. ............... 510/302; 510/303; 510/311; 510/276

(58) Field of Search ............... 510/367, 376, 510/307, 311, 302; 8/111, 1.1

(56) References Cited

U.S. PATENT DOCUMENTS

| 5,882,355 | A | * | 3/1999 | Koek | 8/111 |
|---|---|---|---|---|---|
| 6,059,844 | A | * | 5/2000 | Koek | 8/111 |
| 6,140,294 | A | | 10/2000 | Delroisse et al. | |
| 6,165,963 | A | | 12/2000 | Delroisse et al. | |
| 6,242,409 | B1 | * | 6/2001 | Appel et al. | 510/376 |
| 6,245,115 | B1 | * | 6/2001 | Appel et al. | 8/111 |

FOREIGN PATENT DOCUMENTS

| DE | 197 44 122 | 4/1997 | |
|---|---|---|---|
| DE | 19721886 | 5/1997 | |
| EP | 0 909 809 | 4/1999 | |
| WO | 95/27772 | 10/1995 | |
| WO | 95/34628 | 12/1995 | |
| WO | 96/06154 | 2/1996 | |
| WO | 97/38074 | 10/1997 | |
| WO | WO 97/38074 | * 10/1997 | C11D/3/20 |
| WO | 97/48787 | 12/1997 | |
| WO | WO 99/65905 | * 12/1999 | |
| WO | 99/65905 | 12/1999 | |
| WO | 00/12667 | 3/2000 | |
| WO | 00/12808 | 3/2000 | |
| WO | 00/29537 | 5/2000 | |

* cited by examiner

Primary Examiner—Yogendra N. Gupta
Assistant Examiner—John M. Petruncio
(74) Attorney, Agent, or Firm—Milton L. Honig

(57) ABSTRACT

The invention relates to catalytically bleaching substrates, especially laundry fabrics, with atmospheric oxygen or air. A method of bleaching a substrate is provided that comprises applying to the substrate, in an aqueous medium, a specified ligand from a selected class which forms a complex with a transition metal, the complex catalysing bleaching of the substrate by atmospheric oxygen. Also provided is an aqueous bleaching composition substantially devoid of peroxygen bleach or a peroxy-based or -generating bleach system. Also provided is a method of treating a textile such as a laundry fabric whereby a complex catalyses bleaching of the textile by atmospheric oxygen after the treatment. The catalyst may be used in dry form, or in a liquor that is then dried, such as an aqueous spray-on fabric treatment fluid or a wash liquor for laundry cleaning, or a non-aqueous dry cleaning fluid or spray-on aerosol fluid. The method can confer cleaning benefits to the textile after the treatment. Also provided is a dry textile having a catalyst applied or deposited thereon, whereby bleaching by atmospheric oxygen is catalysed on the textile.

11 Claims, No Drawings

COMPOSITION AND METHOD FOR BLEACHING A SUBSTRATE

This invention relates to compositions and methods for catalytically bleaching substrates with atmospheric oxygen, more particularly using a defined class of ligand or complex as catalyst, and further relates to ligands and complexes useful in such compositions and methods. This invention also relates to a method of treating textiles, such as laundry fabrics, using the defined class of ligand or complex as catalyst, more specifically to a method whereby bleaching by atmospheric oxygen is catalysed after the treatment.

Peroxygen bleaches are well known for their ability to remove stains from substrates. Traditionally, the substrate is subjected to hydrogen peroxide, or to substances which can generate hydroperoxyl radicals, such as inorganic or organic peroxides. Generally, these systems must be activated. One method of activation is to employ wash temperatures of 60° C. or higher. However, these high temperatures often lead to inefficient cleaning, and can also cause premature damage to the substrate.

A preferred approach to generating hydroperoxyl bleach radicals is the use of inorganic peroxides coupled with organic precursor compounds. These systems are employed for many commercial laundry powders. For example, various European systems are based on tetraacetyl ethylenediamine (TAED) as the organic precursor coupled with sodium perborate or sodium percarbonate, whereas in the United States laundry bleach products are typically based on sodium nonanoyloxybenzenesulfonate (SNOBS) as the organic precursor coupled with sodium perborate.

Precursor systems are generally effective but still exhibit several disadvantages. For example, organic precursors are moderately sophisticated molecules requiring multi-step manufacturing processes resulting in high capital costs. Also, precursor systems have large formulation space requirements so that a significant proportion of a launder powder must be devoted to the bleach components, leaving less room for other active ingredients and complicating the development of concentrated powders. Moreover, precursor systems do not bleach very efficiently in countries where consumers have wash habits entailing low dosage, short wash times, cold temperatures and low wash liquor to substrate ratios.

Alternatively, or additionally, hydrogen peroxide and peroxy systems can be activated by bleach catalysts, such as by complexes of iron and the ligand N4Py (i.e. N,N-bis(pyridin-2-yl-methyl)-bis(pyridin-2-yl)methylamine) disclosed in WO95/34628, or the ligand Tpen (i.e. N,N,N',N'-tetra(pyridin-2-yl-methyl)ethylenediamine) disclosed in WO97/48787. According to these publications, molecular oxygen may be used as the oxidant as an alternative to peroxide generating systems. However, no role in catalysing bleaching by atmospheric oxygen in an aqueous medium is reported.

It has long been thought desirable to be able to use atmospheric oxygen (air) as the source for a bleaching species, as this would avoid the need for costly hydroperoxyl generating systems. Unfortunately, air as such is kinetically inert towards bleaching substrates and exhibits no bleaching ability. Recently some progress has been made in this area. For example, WO 97/38074 reports the use of air for oxidising stains on fabrics by bubbling air through an aqueous solution containing an aldehyde and a radical initiator. A broad range of aliphatic, aromatic and heterocyclic aldehydes is reported to be useful, particularly para-substituted aldehydes such as 4-methyl-. 4-ethyl- and 4-isopropyl benzaldehyde, whereas the range of initiators disclosed includes N-hydroxysuccinimide, various peroxides and transition metal coordination complexes.

However, although this system employs molecular oxygen from the air, the aldehyde component and radical initiators such as peroxides are consumed during the bleaching process. These components must therefore be included in the composition in relatively high amounts so as not to become depleted before completion of the bleaching process in the wash cycle. Moreover, the spent components represent a waste of resources as they can no longer participate in the bleaching process.

Accordingly, it would be desirable to be able to provide a bleaching system based on atmospheric oxygen or air that does not rely primarily on hydrogen peroxide or a hydroperoxyl generating system, and that does not require the presence of organic components such as aldehydes that are consumed in the process. Moreover, it would be desirable to provide such a bleaching system that is effective in aqueous medium.

It may also be noted that the known art teaches a bleaching effect only as long as the substrate is being subjected to the bleaching treatment. Thus, there is no expectation that hydrogen peroxide or peroxy bleach systems could continue to provide a bleaching effect on a treated substrate, such as a laundry fabric after washing and drying, since the bleaching species themselves or any activators necessary for the bleaching systems would be assumed to be removed from the substrate, or consumed or deactivated, on completing the wash cycle and drying.

It would be therefore also be desirable to be able to treat a textile such that, after the treatment is completed, a bleaching effect is observed on the textile. Furthermore, it would be desirable to be able to provide a bleach treatment for textiles such as laundry fabrics whereby residual bleaching occurs when the treated fabric has been treated and is dry.

We have found that a selected class of ligand or complex is surprisingly effective in catalysing the bleaching of substrates using atmospheric oxygen or air. Furthermore, we have found certain novel ligands which are useful in the bleaching of substrates using atmospheric oxygen or air.

Accordingly, in a first aspect, the present invention provides a bleaching composition comprising, in an aqueous medium, atmospheric oxygen and a ligand which forms a complex with a transition metal, the complex catalysing bleaching of a substrate by the atmospheric oxygen, wherein the aqueous medium is substantially devoid of peroxygen bleach or a peroxy-based or -generating bleach system. The medium is therefore preferably insensitive or stable to catalase, which acts on peroxy species.

In a second aspect, the present invention provides a method of bleaching a substrate comprising applying to the substrate, in an aqueous medium, a ligand which forms a complex with a transition metal, the complex catalysing bleaching of the substrate by atmospheric oxygen.

Furthermore, in a third aspect, the present invention provides the use of a ligand which forms a complex with a transition metal as a catalytic bleaching agent for a substrate in an aqueous medium substantially devoid of peroxygen bleach or a peroxy-based or -generating bleach system the complex catalysing bleaching of the substrate by the atmospheric oxygen.

We have also found that certain ligands or complexes of this class are surprisingly effective in catalysing bleaching of the substrate by atmospheric oxygen after treatment of the substrate.

Accordingly, in a fourth aspect, the present invention provides a method of treating a textile by contacting the textile with a ligand which forms a complex with a transition metal, whereby the complex catalyses bleaching of the textile by atmospheric oxygen after the treatment.

In a fifth aspect, the present invention provides a dry textile having a ligand as defined above applied or deposited thereon, whereby bleaching by atmospheric oxygen is catalysed on the textile.

In further aspects, the present invention provides ligands and complexes, as defined further below.

Advantageously, the method according to the present invention permits all or the majority of the bleaching species in the medium (on an equivalent weight basis) to be derived from atmospheric oxygen. Thus, the medium can be made wholly or substantially devoid of peroxygen bleach or a peroxy-based or -generating bleach system. Furthermore, the complex is a catalyst for the bleaching process and, as such, is not consumed but can continue to participate in the bleaching process. The catalytically activated bleaching system of the type in accordance with the present invention, which is based on atmospheric oxygen, is therefore both cost-effective and environmentally friendly. Moreover, the bleaching system is operable under unfavourable wash conditions which include low temperatures, short contact times and low dosage requirements. Furthermore, the method is effective in an aqueous medium and is therefore particularly applicable to bleaching of laundry fabrics. Therefore, whilst the composition and method according to the present invention may be used for bleaching any suitable substrate, the preferred substrate is a laundry fabric. The bleaching method may be carried out by simply leaving the substrate in contact with the medium for a sufficient period of time. Preferably, however, the aqueous medium on or containing the substrate is agitated.

An advantage of the method according to the fourth aspect of the invention is that, by enabling a bleaching effect even after the textile has been treated, the benefits of bleaching can be prolonged on the textile. Furthermore, since a bleaching effect is conferred to the textile after the treatment, the treatment itself, such as a laundry wash cycle, may for example be shortened. Moreover, since a bleaching effect is achieved by atmospheric oxygen after treatment of the textile, hydrogen peroxide or peroxy-based bleach systems can be omitted from the treatment substance.

The ligand may be present as a preformed complex of a ligand and a transition metal. Alternatively, the composition may comprise a free ligand that complexes with a transition metal already present in the water or that complexes with a transition metal present in the substrate. The composition may also be formulated as a composition of a free ligand or a transition metal-substitutable metal-ligand complex, and a source of transition metal, whereby the complex is formed in situ in the medium.

The ligand forms a complex with one or more transition metals in the latter case for example as a dinuclear complex. Suitable transition metals include for example: manganese in oxidation states II–V, iron II–V, copper I–III, cobalt I–III, titanium II–IV, tungsten IV–VI, vanadium II–V and molybdenum II–VI.

The ligand forms a complex of the general formula (A1):

$$[M_aL_kX_n]Y_m \quad (A1)$$

in which:

M represents a metal selected from Mn(II)–(III)–(IV)–(V), Cu(I)–(II)–(III), Fe(II)–(III)–(IV)–(V), Co(I)–(II)–(III), Ti(II)–(III)–(IV), V(II)–(III)–(IV)–(V), Mo(II)–(III)–(IV)–(V)–(VI) and W(IV)–(V)–(VI), preferably selected from Fe(II)–(III)–(IV)–(V);

L represents a ligand as herein defined, or its protonated or deprotonated analogue;

X represents a coordinating species selected from any mono, bi or tri charged anions and any neutral molecules able to coordinate the metal in a mono, bi or tridentate manner, preferably selected from $O^{2-}$, $RBO_2^{2-}$, $RCOO^-$, $RCONR^-$, $OH^-$, $NO_3^-$, $NO$, $S^{2-}$, $RS^-$, $PO_4^{3-}$, $PO_3OR^{3-}$, $H_2O$, $CO_3^{2-}$, $HCO_3^-$, $ROH$, $N(R)_3$, $ROO^-$, $O_2^{2-}$, $O_2^-$, $RCN$, $Cl^-$, $Br^-$, $OCN^-$, $SCN^-$, $CN^-$, $N_3^-$, $F^-$, $I^-$, $RO^-$, $ClO_4^-$, and $CF_3SO_3^-$, and more preferably selected from $O^{2-}$, $RBO_2^{2-}$, $RCOO^-$, $OH^-$, $NO_3^-$, $S^{2-}$, $RS^-$, $PO_3^{4-}$, $H_2O$, $CO_3^{2-}$, $HCO_3^-$, $ROH$, $N(R)_3$, $Cl^-$, $Br^-$, $OCN^-$, $SCN^-$, $RCN$, $N_3^-$, $F^-$, $I^-$, $RO^-$, $ClO_4^-$, and $CF_3SO_3^-$;

Y represents any non-coordinated counter ion, preferably selected from $ClO_4^-$, $BR_4^-$, $[MX_4]^-$, $[MX_4]^{2-}$, $PF_6^-$, $RCOO^-$, $NO_3^-$, $RO^-$, $N^+(R)_4$, $ROO^-$, $O_2^{2-}$, $O_2^-$, $Cl^-$, $Br^-$, $F^-$, $I^-$, $CF_3SO_3^-$, $S_2O_6^{2-}$, $OCN^-$, $SCN^-$, $H_2O$, $RBO_2^{2-}$, $BF_4^-$ and $BPh_4^-$, and more preferably selected from $ClO_4^-$, $BR_4^-$, $[FeCl_4]^-$, $PF_6^-$, $RCOO^-$, $NO_3^-$, $RO^-$, $N^+(R)_4$, $Cl^-$, $Br^-$, $F^-$, $I^-$, $CF_3SO_3^-$, $S_2O_6^{2-}$, $OCN^-$, $SCN^-$, $H_2O$ and $BF_4^-$;

a represents an integer from 1 to 10, preferably from 1 to 4;

k represents an integer from 1 to 10;

n represents an integer from 1 to 10, preferably from 1 to 4;

m represents zero or an integer from 1 to 20, preferably from 1 to 8; and each R independently represents a group selected from hydrogen, hydroxyl, —R' and —OR', wherein R'=alkyl, alkenyl, cycloalkyl, heterocycloalkyl, aryl, heteroaryl or a carbonyl derivative group, R' being optionally substituted by one or more functional groups E, wherein E independently represents a functional group selected from —F, —Cl, —Br, —I, —OH, —OR', —NH$_2$, —NHR', —N(R')$_2$, —N(R')$_{3+}$, —C(O)R', —OC(O)R', —COOH, —COO$^-$ (Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$ (Na$^+$, K$^+$), —P(O)(OH)$_2$, or —P(O)(O$^-$(Na$^+$, K$^+$))$_2$, and preferably each R independently represents hydrogen, optionally substituted alkyl or optionally substituted aryl, more preferably hydrogen or optionally substituted phenyl, naphthyl or $C_{1-4}$-alkyl.

The ligand L is of the general formula (I):

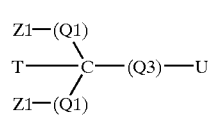

(I)

wherein

Z1 groups independently represent a coordinating group selected from hydroxy, amino, —NHR or —N(R)$_2$ (wherein R=$C_{1-6}$-alkyl), carboxylate, amido, —NH—C(NH)NH$_2$, hydroxyphenyl, a heterocyclic ring optionally substituted by one or more functional groups E or a heteroaromatic ring optionally substituted by one or more functional groups E, the heteroaromatic ring being selected from pyridine, pyrimidine, pyrazine, pyrazole, imidazole, benzimidazole, quinoline, quinoxaline, triazole, isoquinoline, carbazole, indole, isoindole, oxazole and thiazole;

Q1 and Q3 independently represent a group of the formula:

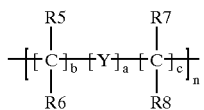

wherein $5 \geq a+b+c \geq 1$; $a=0-5$; $b=0-5$; $c=0-5$; $n=0$ or $1$ (preferably n=0);

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent C$_{1-6}$-alkylene optionally substituted by C$_{1-4}$-alkyl, —F, —Cl, —Br or —I;

T represents a non-coordinated group selected from hydrogen, hydroxyl, halogen, —R and —OR, wherein R represents alkyl, alkenyl, cycloalkyl, heterocycloalkyl, aryl, arylalkyl, heteroaryl or a carbonyl derivative group, R being optionally substituted by one or more functional groups E (preferably T=—H, —OH, methyl, methoxy or benzyl);

U represents either a non-coordinated group T independently defined as above or a coordinating group of the general formula (II), (III) or (IV):

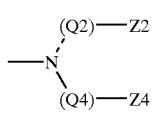 (II)

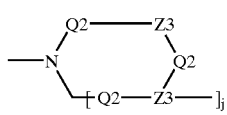 (III)

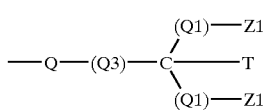 (IV)

wherein

Q2 and Q4 are independently defined as for Q1 and Q3;

Q represents —N(T)— (wherein T is independently defined as above), or an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;

Z2 is independently defined as for Z1;

Z3 groups independently represent —N(T)— (wherein T is independently defined as above);

Z4 represents a coordinating or non-coordinating croup selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups E, or Z4 represents a group of the general formula (IIa):

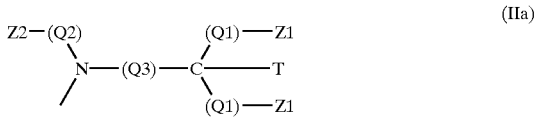 (IIa)

and $1 \leq j < 4$.

Preferably, Z1, Z2 and Z4 independently represent an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole. More preferably, Z1, Z2 and Z4 independently represent groups selected from optionally substituted pyridin-2-yl, optionally substituted imidazol-2-yl, optionally substituted imidazol-4-yl, optionally substituted pyrazol-1-yl, and optionally substituted quinolin-2-yl. Most preferred is that Z1, Z2 and Z4 each represent optionally substituted pyridin-2-yl.

The groups Z1, Z2 and Z4 if substituted, are preferably substituted by a group selected from C$_{1-4}$-alkyl, aryl, arylalkyl, heteroaryl, methoxy, hydroxy, nitro, amino, carboxyl, halo, and carbonyl. Preferred is that Z1, Z2 and Z4 are each substituted by a methyl group. Also, we prefer that the Z1 groups represent identical groups.

The groups R5, R6, R7, R8 preferably independently represent a group selected from —H, hydroxy-C$_0$–C$_{20}$-alkyl, halo-C$_0$–C$_{20}$-alkyl, nitroso, formyl-C$_0$–C$_{20}$-alkyl, carboxyl-C$_0$–C$_{20}$-alkyl and esters and salts thereof, carbamoyl-C$_0$–C$_{20}$-alkyl, sulfo-C$_0$–C$_{20}$-alkyl and esters and salts thereof, sulfamoyl-C$_0$–C$_{20}$-alkyl, amino-C$_0$–C$_{20}$-alkyl, aryl-C$_0$–C$_{20}$-alkyl, C$_0$–C$_{20}$-alkyl, alkoxy-C$_0$–C$_8$-alkyl, carbonyl-C$_0$–C$_6$-alkoxy, and C$_0$–C$_{20}$-alkylamide.

Each Q1 preferably represents a covalent bond or C1–C4-alkylene, more preferably a covalent bond, methylene or ethylene, most preferably a covalent bond.

Group Q preferably represents a covalent bond or C1–C4-alkylene, more preferably a covalent bond.

Non-coordinated group T preferably represents hydrogen, hydroxy, methyl, ethyl, benzyl, or methoxy.

In one aspect of the present invention, the group U in formula (I) represents a coordinating group of the general formula (II):

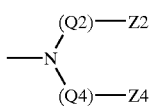

(II)

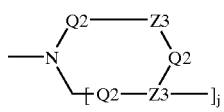

(III)

wherein j is 1 or 2, preferably 1.

According to this aspect, each Q2 preferably represents —(CH$_2$)$_n$—(n=24), and each Z3 preferably represents —N(R)— wherein R=—H or C$_{1-4}$-alkyl, preferably methyl.

In preferred embodiments of this aspect, L represents a ligand selected from:

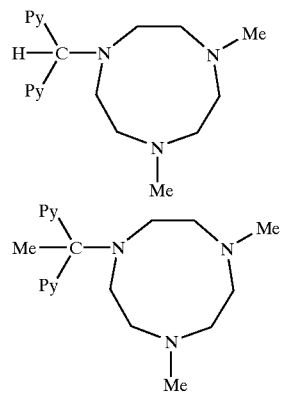

wherein —Py represents pyridin-2-yl.

In yet another aspect of the present invention, the group U in formula (I) represents a coordinating group of the general formula (IV):

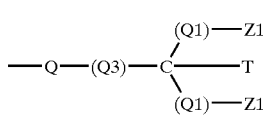

(IV)

In this aspect, Q preferably represents —N(T)— (wherein T=—H, methyl, or benzyl) or pyridin-diyl.

In preferred embodiments of this aspect, L represents a ligand selected from:

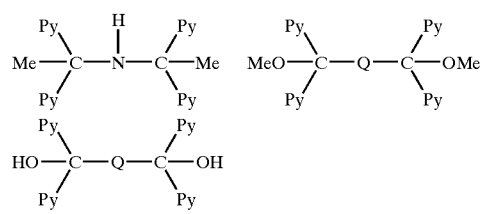

wherein —Py represents pyridin-2-yl, and —Q— represents pyridin-2,6-diyl.

In a further aspect, the present invention provides a ligand L as defined above, with the proviso that T in formula (I) is not benzyl.

In a further aspect, the present invention provides a complex (A1) as defined above, with the proviso that T in formula (I) is not benzyl.

In a further aspect, the present invention provides a ligand as defined above, with the proviso that U represents a non-coordinated group T or a coordinated group of the formula (II) or (III), and if U represents a coordinating group According to this aspect, it is preferred that Z2 represents an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole, more preferably optionally substituted pyridin-2-yl or optionally substituted benzimidazol-2-yl.

It is also preferred, in this aspect, that Z4 represents an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole, more preferably optionally substituted pyridin-2-yl, or an non-coordinating group selected from hydrogen, hydroxy, alkoxy, alkyl, alkenyl, cycloalkyl, aryl, or benzyl.

In preferred embodiments of this aspect, the ligand L is selected from:

1,1-bis(pyridin-2-yl)-N-methyl-N-(pyridin-2-ylmethyl)methylamine 1,1-bis(pyridin-2-yl)-N,N-bis(6-methyl-pyridin-2-ylmethyl)methylamine 1,1-bis(pyridin-2-yl)-N,N-bis(5-carboxymethyl-pyridin-2-ylmethyl)methylamine 1,1-bis(pyridin-2-yl)-1-benzyl-N,N-bis(pyridin-2-ylmethyl)methylamine 1,1-bis(pyridin-2-yl)-N,N-bis(benzimidazol-2-ylmethyl)methylamine In a variant of this aspect, the group Z4 in formula (II) represents a group of the general formula (IIa):

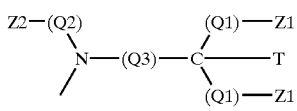

(IIa)

In this variant, Q4 preferably represents optionally substituted alkylene, preferably —CH$_2$—CHOH—CH$_2$— or —CH$_2$—CH$_2$—CH$_2$—. In a preferred embodiment of this variant, L represents the ligand:

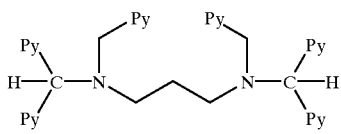

wherein —Py represents pyridin-2-yl.

In another aspect of the present invention, the group U in formula (I) represents a coordinating group of the general formula (III):

of formula (II) and Z1=Z2=Z4=unsubstituted pyridin-2-yl, T is not hydrogen, methyl or benzyl.

In preferred embodiments of this aspect, the ligand is selected from:

1,1-bis(pyridin-2-yl)-N-methyl-N(pyridin-2-ylmethyl) methylamine;

1,1-bis(pyridin-2-yl)-N,N-bis(6-methyl-pyridin-2-ylmethyl)methylamine;

1,1-bis(pyridin-2-yl)-N,N-bis(5-carboxymethyl-pyridin-2-yl)methylamine;

1,1-bis(pyridin-2-yl)-N,N-bis(benzimidazol-2-ylmethyl)methylamine;

2,6-bis(pyridin-2-ylmethyl)-1,1,7,7-tetrakis(pyridin-2-yl)-2,6-diazaheptane; or a ligand selected from:

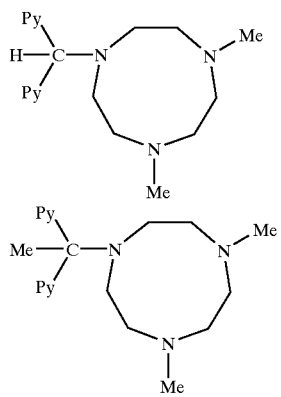

wherein —Py represents pyridin-2-yl.

In a further aspect, the present invention provides a transition-metal complex of the general formula (A1):

$$[M_a L_k X_n] Y_m \quad (A1)$$

in which:

M represents a metal selected from Mn(II)–(III)–(IV)–(V), Cu(I)–(II)–(III), Fe(II)–(III)–(IV)–(V), Co(I)–(II)–(III), Ti(II)–(III)–(IV), V(II)–(III)–(IV)–(V), Mo(II)–(III)–(IV)–(V)–(VI) and W(IV)–(V)–(VI);

X represents a coordinating species selected from any mono, bi or tri charged anions and any neutral molecules able to coordinate the metal in a mono, bi or tridentate manner;

Y represents any non-coordinated counter ion;

a represents an integer from 1 to 10;

k represents an integer from 1 to 10;

n represents an integer from 1 to 10;

m represents zero or an integer from 1 to 20; and

L represents a ligand (or its protonated or deprotonated analogue) as defined above, with the proviso that U represents a non-coordinated group T or a coordinated group of the formula (II) or (III), and if U represents a coordinating group of formula (II) and Z1=Z2=Z4= unsubstituted pyridin-2-yl, T is not hydrogen, methyl or benzyl.

In preferred embodiments of this aspect, the ligand L is selected from:

1,1-bis(pyridin-2-yl)-N-methyl-N(pyridin-2-ylmethyl) methylamine;

1,1-bis(pyridin-2-yl)-N,N-bis(6-methyl-pyridin-2-ylmethyl)methylamine;

1,1-bis(pyridin-2-yl)-N,N-bis(5-carboxmethyl-pyridin-2-yl)methylamine;

1,1-bis(pyridin-2-yl)-N,N-bis(benzimidazol-2-ylmethyl) methylamine;

2,6-bis(pyridin-2-ylmethyl)-1,1,7,7-tetrakis(pyridin-2-yl)-2,6-diazaheptane, or a ligand selected from:

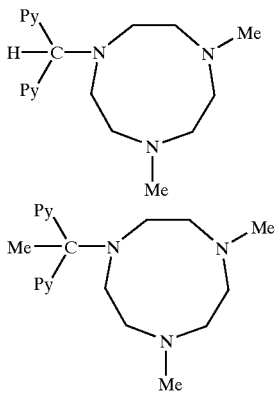

wherein —Py represents pyridin-2-yl.

Preferably, the metal ion in the complex of this aspect is selected from Fe(II)–(III)–(IV). Mn(II)–(III)–(IV)–(V), Cu(I)–(II)–(III) and Co(I)–(II)–(III), more preferably Fe(II)–(III) or Mn(II)–(III)–(IV).

The counter ions Y in formula (A1) balance the charge z on the complex formed by the ligand L, metal M and coordinating species X. Thus, if the charge z is positive, Y may be an anion such as $RCOO^-$, $BPh_4^-$, $ClO_4^-$, $BF_4^-$, $PF_6^-$, $RSO_3^-$, $RSO_4^-$, $SO_4^{2-}$, $NO_3^-$, $F^-$, $Cl^-$, $Br^-$, or $I^-$, with R being hydrogen, optionally substituted alkyl or optionally substituted aryl. If z is negative, Y may be a common cation such as an alkali metal, alkaline earth metal or (alkyl) ammonium cation.

Suitable counter ions Y include those which give rise to the formation of storage-stable solids. Preferred counter ions for the preferred metal complexes are selected from $R^7COO^-$, $ClO_4^-$, $BF_4^-$, $PF_6^-$, $RSO_3^-$ (in particular $CF_3SO_3^-$), $RSO_4^-$, $SO_4^{2-}$, $NO_3^-$, $F^-$, $Cl^-$, $Br^-$, and $I^-$, wherein R represents hydrogen or optionally substituted phenyl, naphthyl or $C_1$–$C_4$ alkyl.

It will be appreciated that the complex (A1) can be formed by any appropriate means, including in situ formation whereby precursors of the complex are transformed into the active complex of general formula (A1) under conditions of storage or use. Preferably, the complex is formed as a well-defined complex or in a solvent mixture comprising a salt of the metal M and the ligand L or ligand L-generating species. Attentively, the catalyst may be formed in situ from suitable precursors for the complex, for example in a solution or dispersion containing the precursor materials. In one such example, the active catalyst may be formed in situ in a mixture comprising a salt of the metal M and the ligand L, or a ligand L-generating species, in a suitable solvent. Thus, for example, if M is iron, an iron salt such as $FeSO_4$ can be mixed in solution with the ligand L, or a ligand L-generating species, to form the active complex. Thus, for example, the composition may formed from a mixture of the ligand L and a metal salt $MX_n$ in which preferably n=1–5, more preferably 1–3. In another such example, the ligand L, or a ligand L-generating species, can be mixed with metal M ions present in the substrate or wash liquor to form the active catalyst in situ. Suitable ligand L-generating species include metal-free compounds or metal coordination complexes that comprise the ligand L and can be substituted by metal M ions to form the active complex according the formula (A1).

The bleaching compositions according to the present invention may be used for laundry cleaning, hard surface cleaning (including cleaning of lavatories, kitchen work surfaces, floors, mechanical ware washing etc.). As is generally known in the art, bleaching compositions are also employed in waste-water treatment, pulp bleaching during the manufacture of paper, leather manufacture, dye transfer inhibition, food processing, starch bleaching, sterilisation, whitening in oral hygiene preparations and/or contact lens disinfection.

In the context of the present invention bleaching should be understood as relating generally to the decolourisation of stains or of other materials attached to or associated with a substrate. However, it is envisaged that the present invention can be applied where a requirement is the removal and/or neutralisation by an oxidative bleaching reaction of malodours or other undesirable components attached to or otherwise associated with a substrate. Furthermore, in the context of the present invention bleaching is to be understood as being restricted to any bleaching mechanism or process that does not require the presence of light or activation by light. Thus, photobleaching compositions and processes relying on the use of photobleach catalysts or photobleach activators and the presence of light are excluded from the present invention.

In typical washing compositions the level of the catalyst is such that the in-use level is from 0.05 $\mu$M to 50 M, with preferred in-use levels for domestic laundry operations falling in the range 0.5 $\mu$M to 100 $\mu$M, more preferably from 1 $\mu$M to 10 $\mu$M. Higher levels may be desired and applied in industrial bleaching processes, such as textile and paper pulp bleaching.

Preferably, the aqueous medium has a pH in the range from pH 6 to 13, more preferably from pH 6 to 11, still more preferably from pH 8 to 11, and most preferably from pH 8 to 10, in particular from pH 9 to 10.

The bleaching composition of the present invention has particular application in detergent formulations, especially for laundry cleaning. Accordingly, in another preferred embodiment, the present invention provides a detergent bleach composition comprising a bleaching composition as defined above and additionally a surface-active material, optionally together with detergency builder.

The bleach composition according to the present invention may for example contain a surface-active material in an amount of from 10 to 50% by weight. The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulfates and sulfonates having alkyl groups containing from about 8 to about 22 carbon atoms, the term "alkyl" being used to include the alkyl portion of higher aryl groups. Examples of suitable synthetic anionic detergent compounds are sodium and ammonium alkyl sulfates, especially those obtained by sulfating higher ($C_8$–$C_{18}$) alcohols produced, for example, from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow or coconut oil fatt acid monoglyceride sulfates and sulfonates; sodium and ammonium salts of sulfuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolysing with a base to produce a random sulfonate; sodium and ammonium ($C_7$–$C_{12}$) dialkyl sulfosuccinates; and olefin sulfonates, which term is used to describe material made by reacting olefins, particularly ($C_{10}$–$C_{20}$) alpha-olefins, with $SO_3$ and then neutralising and hydrolysing the reaction product. The preferred anionic detergent compounds are sodium ($C_{10}$–$C_{15}$) alkylbenzene sulfonates, and sodium ($C_{16}$–$C_{18}$) alkyl ether sulfates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulfoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent bleach composition of the invention will preferably comprise from 1 to 15% wt of anionic surfactant and from 10 to 40% by weight of nonionic surfactant. In a further preferred embodiment, the detergent active system is free from $Ci_6$–$C_{12}$ fatty acid soaps.

The bleach composition of the present invention may also contains a detergency builder, for example in an amount of from about 5 to 80% by weight, preferably from about 10 to 60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. No. 4,144, 226 and U.S. Pat. No. 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P-type as described in EP-A-0,384,070.

In particular, the compositions of the invention may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and water-insoluble crystalline or amorphous aluminosilicate builder materials, each of which can be used as the main builder, either alone or in admixture with minor amounts of other builders or polymers as co-builder.

It is preferred that the composition contains not more than 5% by weight of a carbonate builder, expressed as sodium carbonate, more preferably not more than 2.5% by weight to substantially nil, if the composition pH lies in the lower alkaline region of up to 10.

Apart from the components already mentioned, the bleach composition of the present invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilisers, such as phosphonic acid derivatives (i.e. Dequest® types); fabric softening agents; inorganic salts and alkaline buffering agents, such as sodium sulfate and sodium silicate; and, usually in very small amounts, fluorescent agents; perfumes; enzymes, such as proteases, cellulases, lipases, amylases and oxidases; germicides and colourants.

Transition metal sequestrants such as EDTA, and phosphonic acid derivatives such as EDTMP (ethylene diamine tetra(methylene phosphonate)) may also be included, in addition to the ligand specified, for example to improve the stability sensitive ingredients such as enzymes, fluorescent agents and perfumes, but provided the composition remains bleaching effective. However, the composition according to the present invention containing the ligand, is preferably substantially, and more preferably completely, devoid of transition metal sequestrants (other than the ligand).

Whilst the present invention is based on the catalytic bleaching of a substrate by atmospheric oxygen or air, it will be appreciated that small amounts of hydrogen peroxide or peroxy-based or -generating systems may be included in the composition, if desired. Therefore, by "substantially devoid of peroxygen bleach or peroxy-based or -generating bleach systems" is meant that the composition contains from 0 to 50%, preferably from 0 to 10%, more preferably from 0 to 5%, and optimally from 0 to 2% by molar weight on an oxygen basis, of peroxygen bleach or peroxy-based or -generating bleach systems. Preferably, however, the composition will be wholly devoid of peroxygen bleach or peroxy-based or -generating bleach systems.

Thus, at least 10%, preferably at least 50% and optimally at least 90% of any bleaching of the substrate is effected by oxygen sourced from the air.

According to the fourth aspect, the catalyst may be contacted to the textile fabric in any suitable manner. For example, it may be applied in dry form, such as in powder form, or in a liquor that is then dried, for example as an aqueous spray-on fabric treatment fluid or a wash liquor for laundry cleaning, or a non-aqueous dry cleaning fluid or spray-on aerosol fluid. Other suitable means of contacting the catalyst to the textile may be used, as further explained below.

Any suitable textile that is susceptible to bleaching or one that one might wish to subject to bleaching may be used. Preferably the textile is a laundry fabric or garment.

The bleaching method of the fourth aspect may be carried out by simply leaving the substrate in contact with the catalyst for a sufficient period of time. Preferably, however, the catalyst is in an aqueous medium, and the aqueous medium on or containing the substrate is agitated.

In a preferred embodiment, the treated textile is dried, by allowing it to dry under ambient temperature or at elevated temperatures.

In a particularly preferred embodiment the method according to the fourth aspect is carried out on a laundry fabric using aqueous treatment liquor. In particular the treatment may be effected in, or as an adjunct to, an essentially conventional wash cycle for cleaning laundry. More preferably, the treatment is carried out in an aqueous detergent wash liquor. The catalyst can be delivered into the wash liquor from a powder, granule, pellet, tablet, block, bar or other such solid form. The solid form can comprise a carrier, which can be particulate, sheet-like or comprise a three-dimensional object. The carrier can be dispersible or soluble in the wash liquor or may remain substantially intact. In other embodiments, the catalyst can be delivered into the wash liquor from a paste, gel or liquid concentrate.

It is particularly advantageous that the catalyst used in the method of the fourth aspect makes use of atmospheric oxygen in its bleaching activity. This avoids the requirement that peroxygen bleaches and/or other relatively large quantities of reactive substances need be used in the treatment process. Consequently, only a relatively small quantity of bleach active substance need be employed and this allows dosage routes to be exploited which could previously not be used. Thus, while it is preferable to include the catalyst in a composition that is normally used in a washing process, such as a pre-treatment, main-wash, conditioning composition or ironing aid, other means for ensuring that the catalyst is present in the wash liquor may be envisaged.

For example, it is envisaged that the catalyst can be presented in the form of a body from which it is slowly released during the whole or part of the laundry process. Such release can occur over the course of a single wash or over the course of a plurality of washes. In the latter case it is envisaged that the catalyst can be released from a carrier substrate used in association with the wash process, e.g. from a body placed in the dispenser drawer of a washing machine, elsewhere in the delivery system or in the drum of the washing machine. When used in the drum of the washing machine the carrier can be freely moving or fixed relative to the drum. Such fixing can be achieved by mechanical means, for example by barbs that interact with the drum wall, or employ other forces, for example a magnetic force. The modification of a washing machine to provide for means to hold and retain such a carrier is envisaged similar means being known from the analogous art of toilet block manufacture. Freely moving carriers such as shuttles for dosage of surfactant materials and/or other detergent ingredients into the wash can comprise means for the release of the catalyst into the wash.

In the alternative, the catalyst can be presented in the form of a wash additive that preferably is soluble. The additive can take any of the physical forms used for wash additives, including powder, granule, pellet, sheet, tablet, block, bar or other such solid form or take the form of a paste, gel or liquid. Dosage of the additive can be unitary or in a quantity determined by the user. While it is envisaged that such additives can be used in the main washing cycle, the use of them in the conditioning or drying cycle is not hereby excluded.

The present invention is not limited to those circumstances in which a washing machine is employed, but can be applied where washing is performed in some alternative vessel. In these circumstances it is envisaged that the catalyst can be delivered by means of slow release from the bowl, bucket or other vessel which is being employed, or from any implement which is being employed, such as a brush, bat or dolly, or from any suitable applicator.

Suitable pre-treatment means for application of the catalyst to the textile material prior to the main wash include sprays, pens, roller-ball devices, bars, soft solid applicator sticks and impregnated cloths or cloths containing microcapsules. Such means are well known in the analogous art of deodorant application and/or in spot treatment of textiles. Similar means for application are employed in those embodiments where the catalyst is applied after the main washing and/or conditioning steps have been performed, e.g. prior to or after ironing or drying of the cloth. For example, the catalyst may be applied using tapes, sheets or sticking plasters coated or impregnated with the substance, or containing microcapsules of the substance. The catalyst may for example be incorporated into a drier sheet so as to be activated or released during a tumble-drier cycle, or the substance can be provided in an impregnated or microcapsule-containing sheet so as to be delivered to the textile when ironed.

Throughout the description and claims generic groups have been used, for example alkyl, alkoxy, aryl, Unless otherwise specified the following are preferred group restrictions that may be applied to generic groups found within compounds disclosed herein:

alkyl: linear and branched C1–C8-alkyl, alkenyl: C2–C6-alkenyl, cycloalkyl: C3–C8-cycloalkyl, alkoxy: C1–C6-alkoxy, alkylene: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl, aryl: selected from homoaromatic compounds having a molecular weight under 300, arylene: selected from the group consisting of: 1,2-phenylene; 1,3-phenylene; 1,4-phenylene; 1,2-naphtalenylene; 1,3-naphtalenylene; 1,4-naphtalenylene; 2,3-naphtalenylene; 1-hydroxy-2,3-phenylene; 1-hydroxy-2,4-phenylene; 1-hydroxy-2,5-phenylene; and 1-hydroxy-2,6-phenylene, heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl.

heteroarylene: selected from the group consisting of: pyridindiyl; quinolindiyl; pyrazodiyl; pyrazoldiyl; triazolediyl; pyrazindiyl; and imidazolediyl, wherein the heteroarylene acts as a bridge in the compound via any atom in the ring of the selected heteroarylene, more specifically preferred are: pyridin-2,3-diyl; pyridin-2,4-diyl; pyridin-2,5-diyl; pyridin-2,6-diyl; pyridin-3,4-diyl; pyridin-3,5-diyl; quinolin-2,3-diyl; quinolin-2,4-diyl; quinolin-2,8-diyl; isoquinolin-1,3-diyl; isoquinolin-1,4-diyl; pyrazol-1,3-diyl; pyrazol-3,5-diyl; triazole-3,5-diyl; triazole-1,3-diyl; pyrazin-2,5-diyl; and imidazole-2,4-diyl, heterocycloalkyl: selected from the group consisting of: pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thia-cyclononanyl; 1,4-diaza-7-oxa-cyclononanyl; 1,4,7,10-tetraazacyclododecanyl; 1,4-dioxanyl; 1,4,7-trithia-cyclononanyl; tetrahydropyranyl; and oxazolidinyl, wherein the heterocycloalkyl may be connected to the compound via any atom in the ring of the selected heterocycloalkyl, heterocycloalkylene: selected from the group consisting of: piperidin-1,2-ylene; piperidin-2,6-ylene; piperidin-4,4-ylidene; 1,4-piperazin-1,4-ylene; 1.4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1.4.7-triazacyclonon-2,3-ylene; 1,4,7-triazacyclonon-2,9-ylene; 1,4,7-triazacyclonon-3,8-ylene: 1,4,7-triazacyclonon-2.2-ylidene: 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,5-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thia-cyclonon-1,4-ylene; 1,4-diaza-7-thia-cyclonon-1,2-ylene; 1,4-diaza-7-thia-cyclonon-2,3-ylene; 1,4-diaza-7-thia-cyclonon-6,8-ylene; 1,4-diaza-7-thia-cyclonon-2,2-ylidene; 1,4-diaza-7-oxa-cyclonon-1,4-ylene; 1,4-diaza-7-oxa-cyclonon-1,2-ylene; 1,4-diaza-7-oxa-cyclonon-2,3-ylene; 1,4-diaza-7-oxa-cyclonon-6,8-ylene; 1,4-diaza-7-oxa-cyclonon-2,2-ylidene 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithia-cyclonon-2,3-ylene; 1,4,7-trithia-cyclonon-2,9-ylene; and 1,4,7-trithia-cyclonon-2,2-ylidene, amine: the group $—N(R)_2$ wherein each R is independently selected from: hydrogen; C1–C6-alkyl; C1–C6-alkyl-C6H5; and phenyl, wherein when both R are C1–C6-alkyl both R together may form an —NC3 to an —NC5 heterocyclic ring with any remaining alkyl chain forming an alkyl substituent to the heterocyclic ring.

halogen: selected from the group consisting of: F; Cl; Br and I.

sulfonate: the group —S(O)$_2$OR, wherein R is selected from: hydrogen; C1–C6-alkyl; phenyl; C1–C6-alkyl-C6H5; Li; Na; K; Cs; Mg; and Ca, sulfate: the group —OS(O)$_2$OR, wherein R is selected from: hydrogen; C1–C6-alkyl; phenyl; C1–C6-alkyl-C6H5; Li; Na; K Cs; Mg; and Ca, sulfone: the group —S(O)$_2$R, wherein R is selected from: hydrogen; C1–C6-alkyl; phenyl; C1–C6-alkyl-C6H5 and amine (to give sulfonamide) selected from the group; —NR'2, wherein each R' is independently selected from: hydrogen; C1–C6-alkyl C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, carboxylate derivative: the group —C(O)OR, wherein R is selected from: hydrogen; C1–C6-alkyl; phenyl; C1–C6-alkyl-C6H5; Li; Na; K; Cs; Mg; and Ca, carbonyl derivative: the group —C(O)R, wherein R is selected from: hydrogen; C1–C6-alkyl; phenyl; C1–C6-alkyl-C6H5 and amine (to give amide) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, phosphonate: the group —P(O)(OR)$_2$, wherein each R is independently selected from: hydrogen; C1–C6-alkyl; phenyl; C1–C6-alkyl-C6H5; Li; Na; K; Cs; Mg; and Ca, phosphate: the group —OP(O)(OR)$_2$, wherein each R is independently selected from: hydrogen; C1–C6-alkyl; phenyl; C1–C6-alkyl-C6H5; Li; Na; K; Cs; Mg; and Ca, phosphine: the group —P(R)$_2$, wherein each R is independently selected from: hydrogen; C1–C6-alkyl; phenyl; and C1–C6-alkyl-C6H5, phosphine oxide: the group —P(O)R$_2$, wherein R is independently selected from: hydrogen; C1–C6-alkyl; phenyl; and C1–C6-alkyl-C6H5; and amine (to give phosphonamidate) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring.

Unless otherwise specified the following are more preferred group restrictions that may be applied to groups found within compounds disclosed herein:

alkyl: linear and branched C1–C6-alkyl, alkenyl: C3–C6-alkenyl, cycloalkyl: C6–C8-cycloalkyl, alkoxy: C1–C4-alkoxy, alkylene: selected from the group consisting of: methylene; 1,2-ethylene; 1,3-propylene; butan-2-ol-1,4-diyl; 1,4-butylene; cyclohexane-1,1-diyl; cyclohexan-1,2-diyl; cyclohexan-1,4-diyl; cyclopentane-1,1-diyl; and cyclopentan-1,2-diyl, aryl: selected from group consisting of: phenyl; biphenyl; naphthalenyl; anthracenyl; and phenanthrenyl, arylene: selected from the group consisting of: 1,2-phenylene 1,3-phenylene; 1,4-phenylene; 1,2-naphtalenylene; 1,4-naphtalenylene; 2,3-naphtalenylene and 1-hydroxy-2,6-phenylene, heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl, heteroarylene: selected from the group consisting of: pyridin-2,3-diyl; pyridin-2,4-diyl; pyridin-2,6-diyl; pyridin-3,5-diyl; quinolin-2,3-diyl; quinolin-2,4-diyl; isoquinolin-1,3-diyl; isoquinolin-1,4-diyl; pyrazol-3,5-diyl; and imidazole-2,4-diyl, heterocycloalkyl: selected from the group consisting of: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heterocycloalkyl may be connected to the compound via any atom in the ring of the selected heterocycloalkyl, heterocycloalkylene: selected from the group consisting of: piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrrolidin-2,5-ylene; pyrrolidin-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thia-cyclonon-1,4-ylene; 1,4-diaza-7-thia-cyclonon-2,3-ylene; 1,4-diaza-7-thia-cyclonon-2,2-ylidene; 1,4-diaza-7-oxa-cyclonon-1,4-ylene; 1,4-diaza-7-oxa-cyclonon-2,3-ylene; 1,4-diaza-7-oxa-cyclonon-2,2-ylidene; 1,4-dioxan-2,6-ylene; 1,4-dioxan-2,2-ylidene; tetrahydropyran-2,6-ylene; tetrahydropyran-2,5-ylene; and tetrahydropyran-2,2-ylidene, amine: the group —N(R)$_2$, wherein each R is independently selected from: hydrogen; C1–C6-alkyl; and benzyl, halogen: selected from the group consisting of: F and Cl, sulfonate: the group —S(O)$_2$OR, wherein R is selected from: hydrogen: C1–C6-alkyl; Na; K; Mg; and Ca, sulfate: the group —OS(O)$_2$OR, wherein R is selected from: hydrogen; C1–C6-alkyl; Na; K; Mg; and Ca, sulfone: the group —S(O)$_2$R, wherein R is selected from: hydrogen; C1–C6-alkyl; benzyl and amine selected from the group: —NR'2, wherein each R' is independently selected from: hydrogen; C1–C6-alkyl; and benzyl, carboxylate derivative: the group —C(O)OR, wherein R is selected from hydrogen; Na; K; Mg; Ca; C1–C6-alkyl; and benzyl, carbonyl derivative: the group: —C(O)R, wherein R is selected from: hydrogen; C1–C6-alkyl; benzyl and anine selected from the group: —NR'2, wherein each R' is independently selected from: hydrogen; C1–C6-alkyl; and benzyl, phosphonate: the group —P(O)(OR)$_2$, wherein each R is independently selected from: hydrogen; C1–C6-alkyl; benzyl; Na; K; Mg; and Ca, phosphate: the group —OP(O)(OR)$_2$, wherein each R is independently selected from: hydrogen; C1–C6-alkyl; benzyl; Na; K; Mg: and Ca, phosphine: the group —P(R)$_2$, wherein each R is independently selected from: hydrogen; C1–C6-alkyl; and benzyl, phosphine oxide: the group —P(O)R$_2$, wherein R is independently selected from: hydrogen; C1–C6-alkyl; benzyl and amine selected from the group: —NR'2, wherein each R' is independently selected from: hydrogen; C1–C6-alkyl; and benzyl.

The invention will now be further illustrated by way of the following non-limiting examples:

EXAMPLES

The following compounds were prepared and tested for catalytic bleaching activity using air:

Compound 1: [Fe(L$^1$)(CH$_3$CN)](ClO$_4$)$_2$
L$^1$=1,1bis(pyridin2-yl)-N-methyl-N-(pyridin-2-ylmethyl)methylamine Compound 2: [Fe(L$^2$)(CH$_3$CN)](ClO$_4$)$_2$
L$^2$=1,1-bis(pyridin-2-yl)N,N-bis(6-methyl-pyridin-2-ylmethyl)methylamine Compound 3: [Fe$_2$(L$^3$)(CH$_3$CN)$_2$](ClO$_4$)$_4$
L$^3$=2,6-bis(pyridin-2-ylmethyl)-1,1,7,7-tetrakis(pyridin-2-yl)-2,6-diazaheptane Compound 4: [Fe(L$^4$)(CH$_3$CN)](ClO$_4$)$_2$
L$^4$=1,1-bis(pyridin-2-yl)-1-benzyl-N,N-bis(pyridin-2-ylmethyl)methylamine Compound 5: [Fe(L$^5$)(CH$_3$CN)]ClO$_4$)$_2$
L$^5$=1,1-bis(pyridin-2-yl)-N,N-bis(5-methoxycarbonyl-pyridin-2-ylmethyl)methylamine Compound 6: [Fe(L$^6$)(CH$_3$CN$_3$CN)$_2$](ClO$_4$)$_2$
L$^6$=1-(α,α-bis(pyridin-2-yl))methyl-4,7-dimethyl-1,4,7-triazacyclononane Compound 7: [Fe(L$^7$)(CH$_3$CN)$_2$](ClO$_4$)$_2$
L$^7$=1-(α,α-bis(pyridin-2-yl))ethyl-4,7-dimethyl-1,4,7-triazacyclononane Compound 8: 2,2,4,4-tetrakis(pardin-2-yl)-3-azapentane (=L$^8$)+Fe(ClO$_4$)$_2$ Compound 9: L$^8$+Mn(ClO$_4$)$_2$.6H$_2$O Compound 10: L$^8$+Co(ClO$_4$)$_2$.6H$_2$O Compound 11:
1,1-bis(pyridin-2-yl)-N,N-bis(benzimidazol-2-ylmethyl)methylamine(=L$^9$)

Compound 12: L$^9$+Fe(ClO$_4$)$_2$.6H$_2$O

Compound 13: L$^9$+Mn(ClO$_4$)$_2$.6H$_2$O

Compound 14: L$^9$+Co(ClO$_4$)$_2$.6H$_2$O

Compound 15: L$^9$+Cu(ClO$_4$)$_2$.6H$_2$O

Compound 16: 2,6-bis(methoxy-bis(pyridin-2-yl)methyl)pyridin(=L$^{10}$)+Co(ClO$_4$)$_2$.6H$_2$O Compound 17: 2,6-bis(hydroxy-bis-pyridin-2-yl)-methyl)pyridin(=L$^{11}$)+Co(ClO$_4$)$_2$.6H$_2$O

Syntheses of Compounds

Compound 1

1,1-bis(Pyridin-2-yl)-N-methyl-N-(pyridin-2-ylmethyl) methylamine (L1) (=N-[di(2-Pyridinyl)methyl]-N-methyl-N-(2-pyridinylmethyl)amine)

To di-2-pyridyl methyl amine (1.5 g, 8.1 mmol) was added freshly distilled pyridine-2-carboxaldehyde (900 mg, 8.4 mmol). After shaking the flask, the mixture was allowed to stand for approximately 2 hours. The white solid was collected and washed with cyclohexane to remove traces of unreacted starting material to give pure N-[di(2-pyridinyl)methyl]-N-[(Z)-2-pyridinylmethylidene]amine (2.02 g, 91%). $^1$H-NMR (CDCl$_3$, 300 MHz) δ 6.0 (s, 1H), 7.16 (m, 2H), 7.31 (m, 1H), 7.59 (m, 5H), 8.18 (m, 1H), 8.61 (m, 3H), 8.65 (s, 1H); MS (CI): m/z 275 (M+1).

To a solution of N-[di(2-pyridinyl)methyl]-N-[(Z)-2-pyridinylmethylidene]amine (1.5 g, 5.5 mmol) in methanol (20 ml) was added NaBH$_4$ (0.45 g, 11.8 mmol) in small portions. After stirring at room temperature for 2 hours HCl (aq) is added until the pH<2. After stirring for 30 min 5 N NaOH (aq) is added until the pH>9. The methanol is removed through evaporation and the aqueous layer is extracted with ethyl acetate (3×30 ml). The combined ethyl acetate layers are washed with brine (30 ml) and dried (Na$_2$SO$_4$). Evaporation of the solvent gave N-[di(2-pyridinyl)methyl]-N-(2-pyridinylmethyl)amine (N3Py) (1.35 g, 89%) as a yellow oil. $^1$H-NMR (CDCl$_3$, 300 MHz) δ 3.85 (s, 2H), 5.10 (s, 1H), 7.03 (m, 3H), 7.41 (m, 6H), 8.46 (m, 3H); $^{13}$C NMR (CDCl$_3$, 50 MHz) δ 53.1 (t), 68.9 (d), 121.8 (d), 122.1 (d), 122.2 (d), 122.3 (d), 136.3 (d), 136.5 (d), 149.2 (d), 159.6 (s), 161.2 (s); MS (CI): m/z 277 (M+1).

To a solution of N-[di(2-pyridinyl)methyl]-N-(2-pyridinylmethyl)amine (1.262 g, 4.59 mmol) in 1,2-dichloroethane (35 ml) was added formaldehyde (37% solution in water, 0.45 ml, 6.0 mmol). NaBH(OAc)$_3$ (3.92 g, 18.5 mmol) was added in small portions. After stirring for 7 h at room temperature saturated NaHCO$_{3(aq)}$ (35 ml) was added and the 1,2-dichloroethane layer was separated. The aqueous layer is extracted with CH$_2$Cl$_2$ (3×20 ml). The combined organic layers were washed with 1N NaOH (20 ml) and brine (20 ml), dried (Na$_2$SO$_4$) and the solvent removed in vacuo to give N-[di(2-pyridinyl)methyl]-N-methyl-N-(2-pyridinylmethyl)amine (1.235 g, 4.27 mmol, 93%) as a slightly yellow oil. $^1$H NMR (CDCl$_3$, 300 MHz) δ 2.19 (s, 3H), 3.72 (s, 2H), 4.96 (s, 1H), 7.14 (m, 3H), 7.71 (m, 6H), 8.56 (m, 3H); $^{13}$C NMR (CDCl$_3$, 50 MHz) δ 40.32 (q), 61.04 (t), 77.87 (d), 121.76 (d), 122.10 (d), 122.92 (d), 123.21 (d), 136.29 (d), 136.43 (d), 148.86 (d), 149.22 (d), 159.37 (s), 160.59 (s), MS (CI): m/z 291 (M+1).

[(L1)Fe(CH$_3$CN)$_2$](ClO$_4$)$_2$

To a solution of N-[di(2-pyridinyl)methyl]-N-methyl-N-(2-pyridinylmethyl)amine (198 mg, 0.68 mmol) in acetonitrile (3 ml) was added a solution of Fe(ClO$_4$)$_2$.6H$_2$O (250 mg, 0.69 mmol) in methanol (3 ml). The solution was placed in an ethyl acetate bath and after 2 days [(L1)Fe(CH$_3$CN)$_2$](ClO$_4$)$_2$ (344 mg, 0.55 mmol, 81%) was obtained as dark red crystals. $^1$H NMR (CD$_3$CN, 300 MHz) δ 3.81 (br), 5.17 (br), 6.96 (br), 7.40 (t, J=7.7 Hz), 7.64 (t, J=7.7 Hz), 8.04 (t, J=7.7 Hz), 8.59 (br), 8.70 (br), 8.87 (br). 9.02 (br), 11.26 (br), 11.40 (br); Anal. Calcd. for C$_{22}$H$_{24}$Cl$_2$FeN$_6$O$_8$: C 42.13, H 3.86, N 13.40; found: C 41.98, H 3.78, N 13.27.

Compound 2

1,1-bis(Pyridin-2-yl)-N,N-bis(6-methyl-pyridin-2-ylmethyl)methylamine. 2HClO$_4$ To di-2-pyridyl methyl amine (1.8 g, 10 mmol) was mixed with 5 ml of 5N NaOH in water. To 2.83 g (20 mmol) of 2-picolylchloride (synthesised according to W. Mattes et al., Angew Chem., 75, 235 (1963)) was mixed with 5 ml of 5N NaOH in water. Both mixtures were colled in an ice bath and added together under stirring. Stirring was continued for 4 days at 20° C. The reaction mixture was colled in an ice bath and under stirring 3 ml of 70% HClO$_4$ was added. The salt seperated as a liquid which became solid after scratching with a spatula. The yellow precipitate was washed 2 times 10 ml of water and 2 times of 5 ml of methanol. The compound was recrystallised from hot water and dried under vacuum over siccapent. Yield 3.1 g (52.%); m.p. 168.5° C.

$^1$H NMR (CD$_3$CN, 200 MHz) δ 2.88 (s) 6H; 4.21 (s) 4H; 5.91 (s) 1H: 7.33 (d) 2H; 7.43 (d) 2H; 7.63 (m) 4H; 7.99 (t) 2H; 8.15 (t) 2H; 8.82 (d) 2H. $^{13}$C-NMR: 25.80; 58.34; 75.00; 122.60; 129.00; 129.74; 130.82; 132.00; 145.00; 150.80; 153.80. Anal. Calcd. for C$_{23}$H$_{23}$Cl$_2$N$_5$O$_8$: C 48.6, H 4.1, N 12.3, Cl 12.5%; found: C 48.5, H 4.7, N 11.5, Cl 11.5%.

The corresponding iron complex was synthesised as described for the non-methylated analogue (reference M. Lubben et al., 34, 1512 (1995)).

Compound 3
2,6-bis(Pyridin-2-ylmethyl)-1,1,7,7-tetrakis(pyridin-2-yl)-2,6-diazaheptane (L3)
Dipyridyl-methylchloride To a solution of 9.2 g of dipyridylketone in 200 ml methanol was added 1 g sodium borohydride in small portions over 0.5 h. The reaction was exothermic. After completion of the addition the mix was stirred 15'. TLC analysis showed the conversion to be quantitive. To the mix was added 10 ml of cencentrated hydrochloric acid and the acid solution was concentrated by evaporation in vacuo. Water was added and the acidic water phase is washed with dichloromethane. Now 100 ml of 2N NaOH was added and the resulting alkaline mixture was extracted 3× with dichloromethane. The combined organic layers were dried over sodium sulfate, filtered and evaporated giving 9 g of the dipyridylcarbinol. It was found that the compound degraded slowly and CDCl$_3$, samples were prepared just before measurement.

$^1$H NMR (CDCl$_3$) (ppm): 5.86 (s, 1H, Py2C—H); 7.15 (m, 2H, Py—H); 7.50 (m, 2H, Py—H); 7.62 (m, 2H, Py—H); 8.53 (m, 2H, Py—H) $^{13}$C NMR(CDCl3) (ppm): 76.3, 122.2, 123.6, 137.9, 149.1, 161.9

N,N'-(di-Pyrid-2-yl Methyl)-1,3-diaminopropane

2-Pyridine carboxaldehyde (9.0 g, 84 mmol) was added dropwise to a solution of 1,3-diaminopropane (3.0 g, 40 mmol) in methanol (100 ml). The mixture became hot. After stirring for 30 min. NaBH$_4$ (4.0 g, 105 mmol) was added in portions. After addition of the first 0.9 g, sodium tetraborate. 10 aq (7.0 g, 18 mmol) was added. When the addition was complete it was stirred at ambient temperature for 45 min then evaporated to approx. 50 ml, water added (250 ml) and extracted (×4) with CHCl3. The extracts were washed with saturated NaCl then dried and evaporated to leave a pale yellow oil (9.52 g). This was short path distilled to give a forerun of 140 mg, b.p. up to 160° C./1 mm (discarded) and a main fraction 7.33 g b.p. 160–215° C./1 mm.

$^1$H NMR (CDCl$_3$) (ppm) 1.78 (m, 2H), 2.2 (br s, 2NH), 2.76 (m, 4H), 3.9 (s, 4H), 6.96 (m, 21H), 7.15 (d, 2H), 7.45 (m, 2H), 8.37 (d, 2H); $^{13}$C NMR (CDCl$_3$) 30.19, 47.77, 55.11, 121.59, 121.97, 136.12. 148.97, 159.81.

2,6-bis(Pyridin-2-ylmethyl)-1,1,7,7-tetrakis(pyridin-2-yl)-2,6-diazaheptane (N,N'-Bis(Dipyrid-2-ylmethyl)-N,N'-bis(pyrid-2-ylmethyl)-1,3-diaminio-propanle)

A mixture of 1.7 g dipyridyl-methylchloride (14), 1 g N,N'-bis(pyrid-2-ylmethyl)-1,3-diamino-propane (15) and 0.5 g potassium carbonate in 20 ml acetonitrile was stirred and refluxed under argon for 48 h. TLC (silica/eluent CH2Cl2/MeOH(7N NH3) 90/10) indicated the reaction to be almost complete. The mixture was filtered and evaporated. The residue was chromatographed on silica using dichloromethane with increasing methanol concentration (up to 5%) to give 1.5 g pure product as a yellow/brown glassy gum.

$^1$H NMR (CDCl$_3$) δ (ppm): 1.75 (m, 2H), 2.42 ppm (m, 4H), 3.73 (s, 4H), 5.16 (s, 2H), 7.02 (m, 6H), 7.4–7.6 (multiplets, 12H), 8.38 (m, 2H), 8.46 (m, 4H); $^{13}$C NMR (CDCl$_3$) (ppm): 23.5, 49.5, 57.1, 73.0, 121.6, 121.9, 122.7, 123.6, 136.1, 136.2, 148.8, 149.0, 160.4; ESP-Mass m/z: 615.3 (M+Na)$^+$, 593.4 (M+H)$^+$, 502.3 (M+H—CH2C5H4N), 425.2 (502.3+H—C5H4N).

Fe-complex

To a solution of 0.11 g of the ligand (see above) in 2 ml MeOH and 2 ml acetonitrile was added 0.1 g iron(II) perchlorate hexahydrate and 0.2 g of sodium perchlorate. Ethyl acetate was allowed to diffuse into the mixture for over three days. Dark brown crystals were isolated from the mixture by filtration giving 20 mg of the product after drying. UV/Vis (CH3CN) $λ_{max}$ (ε a.u.): 695 nm (0.038), 493 nm (0.259), 471 nm (0.271), 334 nm (2.95). I.R. (Kbr, cm−1): 3421, 1607, 1447, 1112, 1088, 792, 628.

Compound 4
[Fe(L$^4$)(CH$_3$CN)](ClO$_4$)$_2$
1,1-bis(Pyridin-2-yl)-1-benzyl-N,N-bis(pyridin-2-ylmethyl)methylamine (L4) Compound 4 was Synthesised as Described Elsewhere (EP 0909 809 A2)

Compound 5
1,1-bis(Pyridin-2-yl)-N,N-bis(5-carbocymethyl-pyridin-2-ylmethyl)methylamine (L5)

Methyl 6-methylnicotinate (10 g, 66.2 mmol) was dissolved in dichloromethane (150 ml). 3-Chloroperoxybenzoic acid (17 g, 112 mmol) was added and the mixture was stirred for 3 hours at room temperature. Saturated NaHCO$_3$ solution (200 ml) was added and the mixture was stirred for an additional hour. The dichloromethane layer was separated and the aqueous layer was extracted with dichloromethane (2×100 ml). The combined dichloromethane layers were washed with saturated NaHCO$_3$ (aq) (100 ml), brine (100 ml) and dried (Na$_2$SO$_4$). After evaporation of the solvent methyl 6-(chloromethyl) nicotinate N-oxide (7.8 g, 51.0 mmol) was obtained as a creme colored solid, mp 90.4–90.8° C., which was combined with p-toluenesulfonyl chloride (10.7 g, 56.1 mmol) and dioxane (100 ml) under an Argon atmosphere. The reaction mixture was heated under reflux for 1 night. After cooling to room temperature the solvent was evaporated and the residue dissolved in dichloromethane (200 ml). The solution was washed with saturated Na$_2$CO$_3$ (aq) (2×100 ml), brine (50 ml) and dried (Na$_2$SO$_4$). After evaporation of the solvent the product was purified by column chromatography (SiO2, using hexane/ethyl acetate 10:2.5 as an eluens) to give methyl 6-(chloromethyl)nicotinate (5.71 g, 46% overall yield) as a slightly yellow solid. An analytically pure sample could be obtained by recrstallization from n-hexane, mp 63.5–63.8° C.; $^1$H-NMR (CDCl$_3$) δ 3.94 (s, 3H) 4.70 (s, 2H), 7.58 (d, 1H, J=8.4 Hz), 8.30 (dd, 1H, J=8.1 Hz, J=2.2 Hz), 9.08 (d, 1H, J=1.5 Hz); Anal. Calcd. for C$_8$H$_8$ClNO$_2$: C 51.77, H 4.34, N 7.55; found: C 51.50, H 4.23, N 7.46.

A solution of di(2-pyridinyl)methylamine (555 mg, 3.0 mmol), methyl 6-(chloromethyl)nicotinate (1.7 g, 9.2 mmol) and N,N-diisopropylethylamine (1.6 ml, 9.2 mmol) was placed under argon and heated under reflux for 1 night. After evaporation of the solvent water (10 ml) was added and the product was extracted with ethyl acetate (3×15 ml). The combined organic layers were washed with brine (10 ml), dried (Na$_2$SO$_4$) and the solvent removed in vacuo. Column chromotagraphy (Alox akt. I, ethyl acetate/hexane/triethylamine 10:5:1) afforded 1,1-bis(pyridin-2-yl)-N,N-bis(5-carboxymethyl-pyridin-2-ylmethyl)methylamine (548 mg, 1.2 mmol, 40%) as a slightly yellow oil. $^1$H NMR (CDCl$_3$, 300 MHz) δ 3.90 (s, 6H), 4.04 (s, 4H), 5.32 (s, 1H), 7.13 (m, 2H), 7.60 (m, 2H), 8.16 (dd, 2H, J=8.05 Hz, J=2.2 Hz), 8.56 (d, 2H, J=4.8 Hz) 9.06 (d, 2H, J=1.8 Hz); $^{13}$C NMR (CDCl$_3$, 50 MHz) δ 52.03 (q), 57.28 (t), 72.32 (d), 122.16 (d), 122.39 (d), 123.82 (d), 124.10 (s), 136.24 (d), 137.22 (d), 149.25 (d), 150.15 (d), 159.48 (s), 164.33 (s), 165.69 (s); MS (CI): m/z 484 (M+1).

[(L5)Fe(CH$_3$CN)](ClO$_4$)$_2$

To a solution of 1,1-bis(pyridin-2-yl)-N,N-bis(5-carboxymethyl-pyridin-2-ylmethyl)methylamine (72 mg, 0.15 mmol) in acetonitrile (1.5 ml) was added a solution of Fe(ClO$_4$)$_2$.6H$_2$O (55 mg, 0.15 mmol) in methanol (1.5 ml). The solution was placed in an ethyl acetate bath and after 3 days [(L5)Fe(CH$_3$CN)](ClO$_4$)$_2$ (96 mg, 0.12 mmol, 82%) was obtained as dark red crystals. $^1$H NMR (CD$_3$CN, 300 MHz) δ 3.94 (s, 6H), 4.39 (d, 2H, J=18.7 Hz), 4.51 (d, 2H, J=19.0 Hz), 6.40 (s, 1H), 7.21 (d, 2H, J=8.1 Hz), (t, 2H J=6.2 Hz), 7.91 (m, 4H), 8.14 (d, 2H, 8.1 Hz), 8.91 (d, 2H, J=4.8 Hz), 9.48 (s, 2H); Anal. calcd for C$_{29}$H$_{28}$Cl$_2$Fe$_1$N$_6$O$_{12}$: C 44.69, H 3.62, N 10.78; found: C 44.28, H 3.69, N 10.63.

Compound 6
1-[di(2-Pyridin-2-yl)methyl]-4,7-dimethyl-1,4,7-triazacyclonane (L6)

To a solution of 80 mL n-BuLi in hexanes (2.5 M, 0.2 mol) was added 2-pyridylbromide (31.6 gram 0.2 mol) in 100 mL of ether at –80° C.—60° C. The suspension was stirred for 1 h, and the temperature was allowed to rise to –45° C. Subsequently 2-pyridinecarboxaldehyde (21.42 gram 0.2 mol) in of ether (100 mL) was added during 30 min. To the thick slurry was added additional THF (200 mL) and the mixture was stirred for 1.5 h at –40° C.—–30° C. and then the mixture was allowed to warm up to –10° C. The mixture was poured into water (200 ml) and acidified with 2 M HCl to pH=1–2 and the layers were separated. The aqueous layer was extracted twice with ether (100 mL) and neutralized with saturated Na$_2$CO$_{3(aq)}$ to pH=8. The aqueous layer was extracted CH$_2$Cl$_2$ (3×100 ml). Drying (Na$_2$SO$_4$) and evaporation of the solvent yielded a brown oil. Vacuum distillation (118° C., 0.2 mmHg) afforded di(2-pyridinyl) methanol (19.42 gram, 104.4 mmol, 52%) as a yellow oil. $^1$H-NMR (200 MHz. CDCl$_3$) δ 5.88 (s, 2H), 7.11–7.19 (m, 2H), 7.47–7.67 (m, 4H). 8.50–8.54 (m, 2H). $^{13}$C-NMR (50.3 MHz, CDCl$_3$) δ 75.0 (d), 121.0 (d), 122.5 (d), 136.8 (d), 1448.1 (d), 160.7 (s).

To di(2-pyridinyl)methanol (8.73 g, 46.94 mmol) in CH$_3$CN (100 ml) at 0° C. was added a solution of PPh$_3$ (14.77 gram, 56.32 mmol) in of CCl$_4$ (80 mL) in 1.5 h. The solution was left standing overnight. After addition of MeOH (10 ml) and stirring for 15 min the mixture was concentrated in vacuum to ca 50 ml. To the residue was added of water (100 ml) and the mixture was acidified with 2M HCl to pH=1, and washed twice with 100 ml of CHCl$_3$, the aqueous layer was neutralized with K$_2$CO$_3$ and extracted 4 times with 75 ml of ether. Drying and evaporation of the solvent yielded 2-[chloro(2-pyridinyl)methyl]pyridine (5.41 gram, 56%) as a pale brown solid. Analytically pure material was obtained by column chromatography on silica (ether). $^1$H-NMR (200 MHz, CDCl$_3$) δ 6.20 (s, 1H), 7.14–7.20 (m, 2H), 7.60–7.73 (m, 4H). 8.51–8.54 (m, 2H). $^{13}$C-NMR (50.3 MHz, CDCl$_3$) δ 62.84 (d), 121.3 (d), 121.5 (d), 135.7 (d), 147.7 (d), 156.9 (s). Anal. Cald. for C$_{11}$H$_9$ClN$_2$: C 64.56, H 4.43, Cl 17.32, N 13.69; Found: C 64.48, H 4.45, Cl 17.29, N 13.49.

A solution of bis(2-pyridyl)methyl chloride (170 mg, 0.83 mmol), 1,4-dimethyl-1,4,7-triazacyclonane (155 mg, 0.99 mmol) (ref. Koek et al, J.Chem.Soc., Dalton, Trans, 353 (1996)) and K$_2$CO$_3$ (136 mg, 0.99 mmol) in acetonitrile (10 ml) was placed under Ar and heated under reflux during 16 h. The reaction mixture was poored out in water (20 ml) and brought to pH>10 with NaOH. The aqueous solution was extracted with ethyl acetate (3×15 ml). The combined organic layers were dried (K$_2$CO$_3$) and the solvent was removed in vacuo to give 1-[di(2-pyridinyl)methyl]4,7-dimethyl-1,4,7-triazonane (250 mg, 0.77 mmol, 93%) as a slightly yellow oil. $^1$H NMR (CDCl$_3$, 300 MHz) δ 2.28 (s, 6H), 2.60 (m, 4H), 2.79 (s, 4H), 2.81 (m, 4H), 5.07 (s, 1H), 7.06 (dt, 2H, J=5.1 Hz, J=3.3 Hz), 7.57 (m, 4H), 8.47 (d, 2H, J=4.8 Hz); $^{13}$C NMR (CDCl$_3$, 50 MHz) δ 46.40 (q). 53.96 (t), 56.93 (t). 56.97 (t), 77.70 (d), 121.67 (d), 123.48 (d), 135.96 (d), 148.79 (d), 161.22 (s); HRMS calcd. for C$_{19}$H$_{27}$N$_5$ 325.227, found 325.227.

[(L6)Fe(CH$_3$CN)](ClO$_4$)$_2$

To a solution of 1-[di(2-pyridinyl)methyl]-4,7-dimethyl-1,4,7-triazacyclonane (78 mg, 0.24 mmol) in acetonitrile (2 ml) was added a solution of Fe(ClO$_4$)$_2$.6H$_2$O (95 mg, 0.26 mmol) in methanol (2 ml). The solution was placed in an ethyl acetate bath and after 1 night [(L6)Fe(CH$_3$CN)] (ClO$_4$)$_2$ (0.2 mmol, 85%) was obtained as dark red crystals. $^1$H NMR (CD$_3$CN, 300 MHz) δ 2.73 (s, 6H), 2.86 (m, 6H), 2.96 (m, 6H), 6.09 (s, 1H), 7.33 (m, 2H), 7.79 (d, 2H, J=7.7 Hz), 7.88 (dt, 2H, J=7.7 Hz, J=1.1 Hz), 8.99 (d, 2H, J=5.5 Hz); Anal. calcd for C$_{21}$H$_{30}$Cl$_2$FeN$_6$O$_8$: C 40.60, H 4.87, N 13.53; found: C 40.56, H 4.85, N 13.43.

Compound 7
1-[1,1-di(2-Pyridinyl)ethyl]-4,7-dimethyl-1,4,7-triazacyclonane (L7)

A solution of 1-[di(2-pyridinyl)methyl]-4,7-dimethyl-1,4, 7-triazacyclononane (300 mg, 0.92 mmol) in ether/THF 1:1 (30 ml) was cooled to –80° C. and t-butyllithium (1.5 M in pentane, 0.65 ml, 0.97 mmol) was added. After for stirring for 20 min at –80° C. MeI (60 μL, 0.96 mmol) and the solution was allowed to warm up to room temperature overnight. After removal of the solvent CHCl$_3$ (30 ml) was added and the solution was washed with saturated NaHCO$_3$ $_{(aq)}$ (20 ml) and brine (20 ml), and dried (Na$_2$SO$_4$). Evaporation of the solvent afforded 1-[1,1-di(2-pyridinyl)ethyl]-4,7-dimethyl-1,4,7-triazacyclonane (300 mg, 0.88 mmol, 96%) as a slightly orange solid, which was used without further purification. $^{13}$C NMR (CDCl$_3$, 50 MHz) δ 14.1 (q), 45.4 (q), 50.0 (t), 55.3 (t), 56.6 (t), 60.3 (s), 122.6 (d), 123.8 (d), 136.8 (d), 148.8 (d), 162.6 (s); MS(EI): 339 (M$^+$).

[(L7)Fe(CH$_3$CN)](ClO$_4$)$_2$

To a solution of 1-[1,1-di(2-pyridin-2-yl)ethyl]-4,7-dimethyl-1,4,7-triazacyclonane (112 mg, 0.33 mmol) in acetonitrile (6 ml) was added Fe(ClO$_4$)$_2$.6H$_2$O (143 mg, 0.39 mmol). The solution was placed in an ethyl acetate bath and after 1 night [(L7)Fe(CH$_3$CN)](ClO$_4$)$_2$ (90 mg, 0.14 mmol, 43%) was obtained as red microcrystals.

$^1$ H NMR (CD$_3$CN, 300 MHz) δ 2.24 (s, 3H), 2.67 (m, 6H), 2.70 (s, 6H), 2.97 (m, 6H), 7.33 (m, 2H), 7.63 (m, 2H), 7.90 (m, 2H), 9.01 (d, 2H, J=5.5 Hz).

Compound 8
2,2,4,4-Terrakis(Pyridin-2-yl)-3-azapentane (L8)

Under vigorous stirring and N$_2$-atmosphere, 1 mL of a 3 M solution of MeMgBr in Et$_2$O was added dropwise to a solution of 300 mg (0.749 mmol) of 1,3,3-tris(2-pyridyl)-3H-imidazo[1,5-a]pyridin-4-ium (TPIP) in 20 mL of dry toluene (ref TPIP: M.Renz, et al., *J. Chem. Soc., Chem. Commun.* 1998, 1635.). After 2 h, 2 mL of a saturated NH$_4$Cl solution was added and the solvent evaporated. The residue was dissolved in 10 mL CH$_2$Cl$_2$ and washed with 10 mL of a 2 N NaOH solution. After drying with MgSO$_4$, the solvent was evaporated, the residue dissolved in 1 mL CH$_2$Cl$_2$ and exposed to a pentane atmosphere overnight. 209 mg (73%) of L⁸ were obtained as colorless crystals. ¹H NMR (300 MHz, CDCl₃, 25° C.): d=1.48 (s, 6 H), 5.96 (brs, 1H, N—H), 7.08 (ddd, J=1.7, 4.8, 6.6 Hz, 4H, 2-H), 7.56 (dt, J=1.8, 8.1 Hz, 4H, 3-H), 7.61 (ddd, J=1.1, 1.7, 8.1 Hz, 4H, 4-H), 8.55 (ddd, J=1.1, 1.7, 4.8 Hz, 4H, 1-H).-¹³C NMR (75 MHz, CDCl₃, 25° C.): d=26.3 (q, C-7), 65.6 (s, C-6), 121,5 (d, C-2), 122.3 (d, C4), 136.4 (d, C-3), 148.5 (d, C-1), 168.7 (s, C-5),-FAB-MS, m/z (%): 382 (57) [M+1], 303 (16) [M-py], 183 [dipyridylethyl].

Compound 11
1,1 bis-[Pyridyl-2-yl]-N,N-bis-[benzimidazol-2-yl-methylenyl]-methyl Amine (L9)
Preparation Dipyridyl-methylamine Dipyridyl ketone (25.5 g, 0.138 mol, from Aldrich) and hydroxylamine hydrochloride (20 g) were added to pyridine (120 ml). The mixture was stirred and refluxed for 4 h. allowed to cool to 20° C. and concentrated by evaporation in vacuo. The residue was poored into 1 l of ice water and after stirring a precipitate formed. After 15 min the precipitate was isolated by filtration and dried in vacuo at 60° C. (drying is not strictly necessary as it can be used wet in the next step). This product was used without further purification in the next step.

In a 2l flask the product was dissolved in ethanol (250 ml) and concentrated ammonia (400 ml), water (250 ml) and ammonium acetate (10 g) were added. The mixture was heated to 90° C. while stirring with a mechanical stirrer. Zinc powder (37.5 g) was added in small portions to the stirred mixture over a 1 h period. After the addition was complete stirring was continued for 3 h. TLC (silica, eluent ammonia/butanol 70/30) showed conversion to be complete and the mix was allowed to cool to 20° C. filtered over celite and concentrated. Sodium hydroxide solution (20%, 100 ml) was added to the concentrate and the mixture was extracted three times with ether.

(The aqueous layer should be strongly alkaline, in some cases more extractions were needed to obtain a good yield. The use of CH₂Cl₂ instead of ether is preferred as extraction is more efficient)

The ether layers were combined and washed with saturated sodium chloride solution, dried over sodium sulfate, filtered and evaporated to give 21 g (81.9% if pure) of a light yellow oil ¹H NMR (CDCl₃) (ppm): 2.50 (bs, 2H, NH2); 5.30 (s, 1H, Py2C—H); 7.05 (m, 2H, Py—H); 7.37 (m, 2H, Py—H); 7.58 (m, 2H, Py—H); 8.51 (m, 2H, Py—H). ¹³C NMR (CDCl₃) (ppm): 62.6, 122.0, 122.3, 136.9, 149.4 and 163.0
N2Py-diacetate To a cooled solution of sodium hydroxide (3.5 g in 3 ml water) was added 4.2 chloroacetic acid. Subsequently 3.7 g (20 mmol) of dipyrridylmethane in 6 ml water was added. The reaction was stirred and monitored by TLC (30% ammonia/70% MeOH). After 5 days still starting product was observed and again chloroacetic acid prenuetralized in alkaline was added in a couple of portions over time till TLC indicate that all starting material was converted. After workup a mixture of product. triethylamine (needed to extract the product into an organic phase) and glycolate was obtained. The product was used without further purification. 1,1 bis-[Pyridyl-2-yl]-N,N'-bis-[benzimidazol-2-yl-methylenyl]-methyl Amine To 2.5 g of the mixture obtained as described above, was added 1.4 g o-phenylene diamine and placed in a 195C oil bath. After 25 minutes the mixture was allowed to cool, taken up in dichloromethane and washed with ammonia. The dichloromethane layer was evaporated giving a dark red oil. Chromatography (SiO2, with CH2Cl2/MeOH gradient) gave 0.56 g product.

¹H NMR (CDCl₃) (ppm): 4.0 (s, 4H, CH2); 5.30 (s, 1H, Py2C—H); 7.06 (m, 2H, Py—H); 7.21 (m, 4H, Ar—CH), 7.39 (m, 2H, Py—H); 7.50 (m, 2H, Py—H); 7.60 (m, 4H, Ar—CH), 8.48 (m, 2H, Py—H). ¹³C NMR (CDCl₃) (ppm): 49.3, 72.5, 115.2, 115.6, 122.6, 122.7, 123.0. 124.5, 137.3, 137.9, 138.3, 141.1, 149.1 152.2 and 158.7

Compounds 16 and 17
2,6-bis(Methoxy-bis(pyridin-2-yl)methyl)pyridin (L10) and 2,6-bis(Hydroxy-bis-pyridin-2-yl)-methyl)pyridin (L11) were Synthesised as Published Elsewhere (M. E. de Vries, B. L. Feringa, et al., *Chem Comm*, 1549 (1997).

Experimental

In an aqueous solution containing 10 mM carbonate buffer (pH 10) without and with 0.6 g/l Na-LAS (linear alkylbenzene sulfonate) or containing 10 mM borate buffer (pH 8) without and with 0.6 g/l NaLAS, tomato-soya oil stained cloths (6×6 cm) were added and stirred for 30 minutes at 30° C. (blanks). In a second series of experiments, the same tests were done in the presence of 10 μM of compound 1–7 or 20 μM of ligand L9, L10, or L11 in combination with Mn, Fe, Co or Cu perchlorate salt The cloths were measured immediately after the wash (Table 1) or after 24 h storage in a dark room under ambient conditions (Table 2).

After the wash, the cloths were rinsed with water and subsequently dried at 30° C. and the change in colour was measured immediately after drying with a Linotype-Hell scanner (ex Linotype). The change in colour (including bleaching) is expressed as the ΔE value. The measured colour difference (ΔE) between the washed cloth and the unwashed cloth is defined as follows:

$$\Delta E = [(\Delta L)^2 + (\Delta a)^2 + (\Delta b)^2]^{1/2}$$

wherein ΔL is a measure for the difference in darkness between the washed and unwashed test cloth; Δa and Δb are measures for the difference in redness and yellowness respectively between both cloths. With regard to this colour measurement technique, reference is made to Commission International de l'Eclairage (CIE); Recommendation on Uniform Colour Spaces, colour difference equations, psychometric colour terms, supplement no 2 to CIE Publication, no 15, Colormetry, Bureau Central de la CIE, Paris 1978.

The results are shown in Tables 1 and 2 below:

TABLE 1

Bleach values expressed as ΔE obtained for the tomato stains for the various compounds

|  | pH 8 − LAS | pH 8 + LAS | pH 10 − LAS | pH 10 + LAS |
|---|---|---|---|---|
| Blank | 1 | 2 | 1 | 3 |
| Compound 1 | 1 | 12 | 1 | 4 |
| Compound 2 | 6 | 15 | 2 | 6 |
| Compound 3 | 2 | 12 | 2 | 5 |
| Compound 4 | 16 | 16 | 16 | 16 |
| Compound 5 | 18 | 16 | 6 | 11 |
| Compound 6 | 1 | 6 | 1 | 7 |

TABLE 1-continued

Bleach values expressed as ΔE obtained for the tomato stains for the various compounds

| | pH 8 − LAS | pH 8 + LAS | pH 10 − LAS | pH 10 + LAS |
|---|---|---|---|---|
| Compound 7 | 2 | 10 | 2 | 11 |
| Compound 8 | 3 | 16 | 5 | 19 |
| Compound 9 | 3 | 13 | 5 | 15 |
| Compound 10 | 3 | 9 | 3 | 4 |
| Compound 11 | 13 | 12 | 13 | 18 |
| Compound 12 | 17 | 14 | 8 | 17 |
| Compound 13 | 14 | 11 | 6 | 5 |
| Compound 14 | 11 | 6 | 4 | 8 |
| Compound 15 | 13 | 8 | 8 | 13 |

TABLE 2

Bleach values expressed as ΔE obtained for the tomato stains after storage for 24 h in the dark

| | pH 8 − LAS | pH 8 + LAS | pH 10 − LAS | pH 10 + LAS |
|---|---|---|---|---|
| Blank | 2 | 4 | 2 | 4 |
| Compound 16 | 2 | 15 | 3 | 15 |
| Compound 17 | 5 | 12 | 8 | 13 |

What is claimed is:

1. A method of treating a textile by contacting the textile with a ligand which forms a complex with a transition metal, whereby the complex catalyses bleaching of the textile by atmospheric oxygen without use of aldehydes, wherein at least 50% of any bleaching of the substrate occurs by oxygen sourced from the air and after the treatment, wherein the ligand is represented by general formula (I), or its protonated or deprotonated analogue:

wherein

Z1 groups independently represent a coordinating group selected from hydroxy, amino, —NHR or —N(R)$_2$ (wherein R=C$_{1-6}$-alkyl), carboxylate, amido, —NH—C(NH)NH$_2$, hydroxyphenyl, a heterocyclic ring optionally substituted by one or more functional groups E or a heteroaromatic ring optionally substituted by one or more functional groups E, the heteroaromatic ring being selected from pyridine, pyrimidine, pyrazine, pyrazole, imidazole, benzimidazole, quinoline, quinoxaline, triazole, isoquinoline, carbazole, indole, isoindole, oxazole and thiazole;

Q1 and Q3 independently represent a group of the formula:

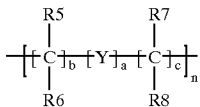

wherein $5 \geq a+b+c \geq 1$; $a=0-5$; $b=0-5$; $c=0-5$; $n=0$ or 1;

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent C$_{1-6}$-alkylene optionally substituted by C$_{1-4}$-alkyl, —F, —Cl, —Br or —I;

E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cyctoatkyl, aryl, arytalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$;

T represents a non-coordinated group selected from hydrogen, hydroxyl, halogen, —R and —OR, wherein R represents alkyl, alkenyl, cyctoatkyl, heterocycloalkyl, aryl, heteroaryt or a carbonyl derivative group, R being optionally substituted by one or more functional groups E;

U represents either a non-coordinated group T independently defined as above or a coordinating group of the general formula (II), (III) or (IV):

-continued

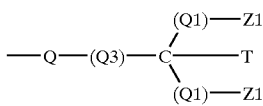
(IV)

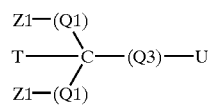
(I)

wherein
Q2 and Q4 are independently defined as for Q1 and Q3;
Q represents —N(T)— (wherein T is independently defined as above), or an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;
Z2 is independently defined as for Z1;
Z3 groups independently represent —N(T)— (wherein T is independently defined as above);
Z4 represents a coordinating or non-coordinating group selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups E, or Z4 represents a group of the general formula (IIa):

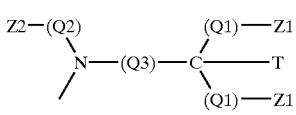
(IIa)

and
$1 \leq j < 4$.

2. A method according to claim 1, wherein the treatment comprises contacting the textile with the ligand in dry form.

3. A method according to claim 2, wherein the treatment comprises contacting the textile with a liquor containing the ligand and then drying.

4. A method according to claim 3, wherein the liquor is an aqueous liquor.

5. A method according to claim 4, wherein the liquor is a spray-on fabric treatment fluid.

6. A method according to claim 4, wherein the liquor is a wash liquor for laundry cleaning.

7. A method according to claim 3, wherein the liquor is a non-aqueous liquor.

8. A method according to claim 7, wherein the liquor is a dry cleaning fluid.

9. A method according to claim 7, wherein the liquor is a spray-on aerosol fluid.

10. A method according to claim 3, wherein the liquor is substantially devoid of peroxygen bleach or a peroxy-based or -generating bleach system.

11. A dry textile having a ligand applied or deposited thereon, whereby bleaching by atmospheric oxygen without use of aldehydes is catalysed on the textile, wherein at least 50% of any bleaching occurs by oxygen sourced from the air, the ligand being defined by the general formula (I), or its protonated or deprotonated analogue:

wherein
Z1 groups independently represent a coordinating group selected from hydroxy, amino, —NHR or —N(R)$_2$ (wherein R=C$_{1-6}$-alkyl), carboxylate, amido, —NH—C(NH)NH$_2$, hydroxyphenyl, a heterocyclic ring optionally substituted by one or more functional groups E or a heteroaromatic ring optionally substituted by one or more functional groups E, the heteroaromatic ring being selected from pyridine, pyrimidine, pyrazine, pyrazole, imidazole, benzimidazole, quinoline, quinoxaline, triazole, isoquinoline, carbazole, indole, isoindole, oxazole and thiazole;
Q1 and Q3 independently represent a group of the formula:

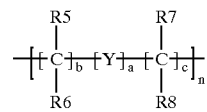

wherein
$5 \geq a+b+c \geq 1$; $a=0-5$; $b=0-5$; $c=0-5$; $n=0$ or $1$;
Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;
R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E,
or R5 together with R6, or R7 together with R8, or both, represent oxygen,
or R5 together with R7 and/or independently R6 together with R8, or R5 together with R8 and/or independently R6 together with R7, represent C$_{1-6}$-alkylene optionally substituted by C$_{1-4}$-alkyl, —F, —Cl, —Br or —I;
E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, -I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$;
T represents a non-coordinated group selected from hydrogen, hydroxyl, halogen, —R and —OR, wherein R represents alkyl, alkenyl, cycloalkyl, heterocycloalkyl, aryl, heteroaryt or a carbonyl derivative group, R being optionally substituted by one or more functional groups E;

U represents either a non-coordinated group T independently defined as above or a coordinating group of the general formula (II), (III) or (IV):

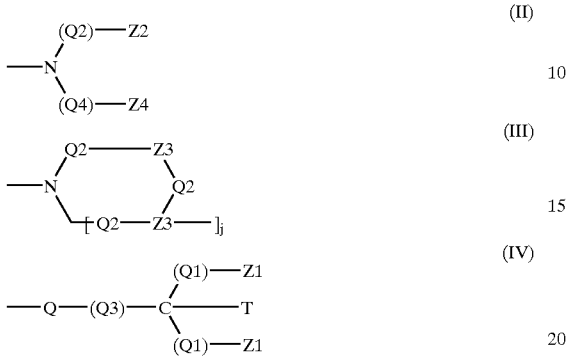

wherein
Q2 and Q4 are independently defined as for Q1 and Q3;
Q represents —N(T)— (wherein T is independently defined as above), or an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;

Z2 is independently defined as for Z1;

Z3 groups independently represent —N(T)— (wherein T is independently defined as above);

Z4 represents a coordinating or non-coordinating group selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups E, or Z4 represents a group of the general formula (IIa):

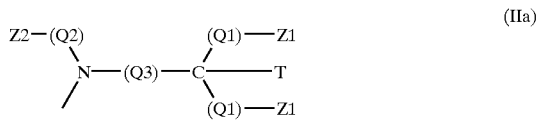

and
$1 \leq j < 4$.

* * * * *